United States Patent [19]

Young

[11] Patent Number: 5,704,785

[45] Date of Patent: Jan. 6, 1998

[54] SALIVA EJECTOR TIP

[76] Inventor: Barry S. Young, 17440 S. W. Cheyenne Way, Tualatin, Oreg. 97062

[21] Appl. No.: 731,326

[22] Filed: Oct. 15, 1996

[51] Int. Cl.$^6$ .............................. A61C 17/06; A61C 17/14
[52] U.S. Cl. ................................................................ 433/91
[58] Field of Search ........................... 433/91, 92, 93, 433/94, 95, 96

[56] References Cited

U.S. PATENT DOCUMENTS

| | | | |
|---|---|---|---|
| 1,124,299 | 1/1915 | Coasd et al. | 433/91 |
| 3,333,340 | 8/1967 | Boisvert | 433/91 |
| 4,049,000 | 9/1977 | Williams | 433/95 X |
| 4,139,012 | 2/1979 | Zahorsky | 433/91 X |
| 4,158,916 | 6/1979 | Adler | 433/91 |

*Primary Examiner*—Nicholas D. Lucchesi
*Attorney, Agent, or Firm*—Trask, Britt & Rossa

[57] ABSTRACT

A saliva ejector tip system, which prevents the problem of backflow when a patient closes his lips around an ejector tip, includes seal-interfering structural features on the outer surface of an ejector tip. A tip holder carried by a saliva elector hand tool couples with the proximal end of the tip in vacuum-tight engagement.

12 Claims, 1 Drawing Sheet

SALIVA EJECTOR TIP

BACKGROUND OF THE INVENTION

1. Field

This invention relates to dental operatory equipment. It is specifically directed to saliva ejectors, and provides an improved ejector tip system for use with saliva ejectors.

2. State of the Art

Saliva ejectors are commonly used in dental operatories. They are typically relatively small hand tools, which are connected to a vacuum source through a hose at a first, proximal, end. They carry an ejector tip holder at a second, distal, end. The tip holder serves as a connector for replaceable ejector tips, and may itself be interchangeable with other holders, each adapted to connect to ejector tips from different vendors. According to conventional practice, ejector tips are interchangeably installed in the tip holder. The ejector tip is positioned appropriately in a patient's mouth, and fluid is evacuated through the ejector under vacuum. A continuous bore through an assembled ejector tip, tip holder, and hand tool provides a path for fluids evacuated from a patient's mouth to a collection vessel or drain.

A typical tip holder is resilient, usually being formed from elastomeric material. The system relies upon a press fit connection between the holder and an ejector tip to retain the tip in proper alignment with a hand tool. Ejector tips are easily attached and replaced in the holder, and a vacuum-tight fit between the hand tool and an ejector tip is maintained. A typical ejector tip is constructed from a soft elastomeric material, and is formed as a simple tube. Such tubular ejector tips may be manufactured through low cost extrusion techniques. A wire may be included within the extruded tip to provide the mechanical properties required to maintain bends manually formed in the ejector tip. For example, a 'J'-shaped bend is often formed in a tip during use to facilitate access to a patient's mouth.

A suction delivery element, such as nozzle with a screen element, is generally attached to the distal end of an ejector tip to prevent a patient's tongue or cheek from sealing the distal end of the bore, thereby stopping vacuum-induced fluid flow. Flow through the bore will then continue so long as the patient's mouth remains partially open. However, patients often inadvertently form a vacuum seal around the ejector tip by closing their lips around the tip. This condition may occur as a consequence of a patient's normal swallow reflex, or when the patient attempts to speak during a procedure. The natural consequence of the creation of such a seal is the backflow of fluids from the ejector into the patient's mouth.

Backflow from a saliva ejector into a dental patient's mouth may serve as a source of cross-contamination among patients. Backflow in low-volume suction lines has been reported to occur when a patient closes his lips around currently available saliva ejector tips. Possible cross-contamination is a matter of concern in the dental practice, particularly in view of the increasing numbers of immuno-compromised patients receiving dental care.

There is an ongoing concern about infection control in dentistry. Therefore there is a need for saliva ejectors that eliminate the problem of backflow. There is also a need for a low cost solution to this problem.

SUMMARY OF THE INVENTION

The present invention provides an improved saliva ejector tip system which avoids the problem of backflow when a patient closes his lips around an ejector tip. A currently preferred embodiment of the improved system makes use of seal-interfering structural features carried by the outer surface of an ejector tip. These external structures interfere with a sealing engagement between a patient's lips and the outer surface of an ejector tip. The tip may be inserted into a tip holder in conventional fashion to effect a mating seal between these two elements. In other instances, a mating seal between the tip and tip holder is unimportant, and a leaking interface is tolerable.

A saliva ejector tip system of this invention generally includes an ejector tip holder element carried at the distal end of a saliva ejector hand tool and an ejector tip having a proximal end, adapted to couple with the tip holder element in vacuum-tight engagement, a distal end and a tubular section between the proximal and distal ends, having an external surface configuration constructed and arranged to interfere with a sealing interface between the tubular section and the lips of a patient circumscribing and pressed against the outer surface of the tubular element.

An ejector tip holder mountable to the distal end of a saliva ejector hand tool may be fashioned to present a socket at the distal end of the hand tool. The proximal end of an ejector tip may be fashioned to be insertable into the socket in either a vacuum seal engagement or a mechanical engagement which permits some fluid flow through the socket outside the tip. The distal end of the tip may terminate in a suction-delivery element, which may comprise an open bore or a suction nozzle. The ejector tip conventionally has an internal bore extending its entire length, and the tubular section generally extends to the proximal tip end. The outer seal-interfering surface configurations conveniently comprise structural elements of approximately constant cross sectional configuration, extending approximately parallel the bore to the proximal end of the tip. The cross sectional configuration of the socket may then be approximately congruent with the cross sectional configuration of the proximal end of the tip.

Certain embodiments provide a conventional mating configuration at the proximal end of the tip. These tips will interface with a conventional tip holder. Other embodiments are characterized by an irregular external cross sectional configuration at their proximal end. A special tip holder may then be fashioned to interface such tips to the hand tool portion of the assembly. The mating inner surface of the tip holder may be configured complementary to the external configuration of the tip. The mutually mating surfaces of the tip and tip holder thereby effect a vacuum-tight connection.

Low production costs and ease of manufacture are achieved by forming the seal-interfering features integrally with the ejector tip. While many surface configurations are operable, approximately linear grooves formed in the exterior surface of the ejector tip approximately parallel its internal bore are presently preferred. These grooves are conveniently formed as the tip is extruded. If a vacuum-tight fit is desired when an ejector tip is mounted for use, a socket in the tip holder may be provided with matching bosses extending inward from the inner surface of the socket to register with the linear grooves of the tip.

DETAILED DESCRIPTION OF THE ILLUSTRATED EMBODIMENT

Figure 1:
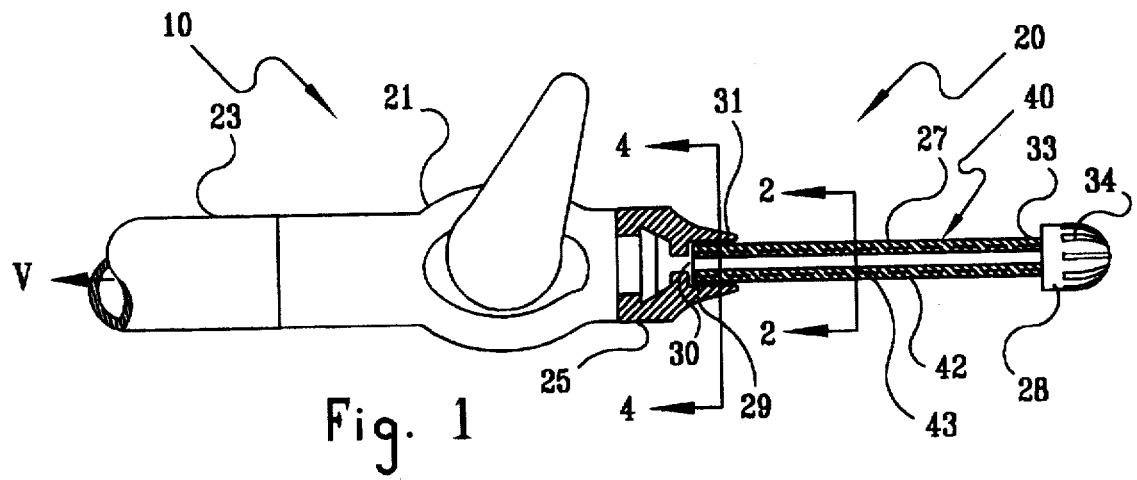
FIG. 1 is a side elevation view, partially in cross section, of a saliva ejector assembly embodying the present invention.

FIG. 1 illustrates a typical saliva ejector assembly, generally indicated 10, incorporating a saliva ejector tip system, generally indicated 20, of the present invention. The assembly 10 comprises a hand tool unit 21 connected at its proximal end to a hose 23, which is plumbed to a vacuum source (not shown). The distal end of the hand tool 21 is fitted with an ejector tip system 20, which includes an ejector tip holder 25, an ejector tip 27, and a specialized suction delivery nozzle 28. The proximal end 29 of the ejector tip 27 is friction fit into a socket 30 carried at the distal end 31 of the holder 25, and the distal end 33 of the ejector tip 27 is capped in turn by the nozzle 28. The nozzle 28 terminates in a screen structure 34.

The tip 27 includes a tubular section, generally 40, between its distal 33 and proximal 29 ends. Approximately linear groove 42 are arranged between ridges 43 on the outer cylindrical surface of the ejector tip 27. As illustrated, these grooves 42 extend along the full length of the section 40 between the nozzle 28 and the proximal end 29 of the tip 27. The particular ejector tip 27 illustrated is extruded from elastomeric material, and includes a co-extruded embedded wire 45. The tip 27 may thus be bent into a desired practical configuration, and the wire will resist the natural memory of the elastomeric material. Otherwise, the tip 27 would tend to return to its straight orientation. The cross sectional configuration of the tubular section 40 is approximately constant along it length, due to its method of manufacture.

Figures 2, 3:
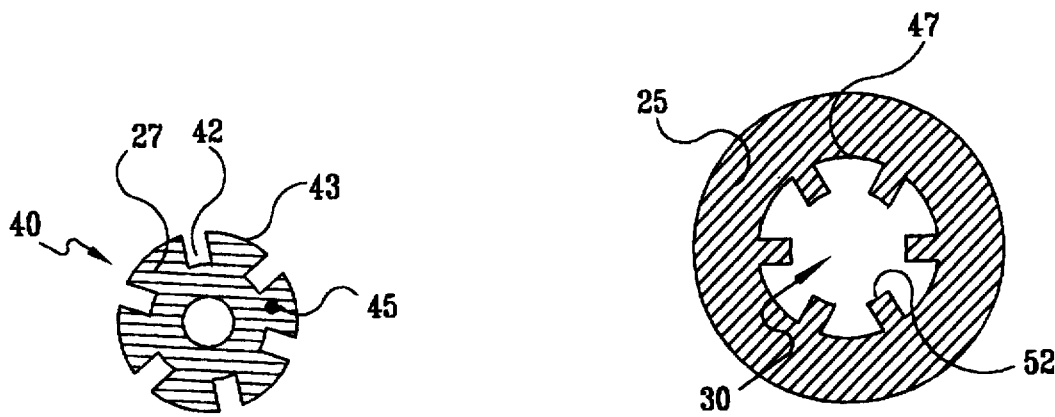
FIG. 2 is an enlarged cross sectional view of the tip component of the assembly of FIG. 1, taken along section line 2—2, viewed in the direction of the arrows and eliminating the other components of the assembly.
FIG. 3 is an enlarged cross sectional view of a tip holder component of the assembly of FIG. 1, taken at the section line 4—4 and viewed in the direction of the arrows, but eliminating the other components of the assembly.
Figure 4:
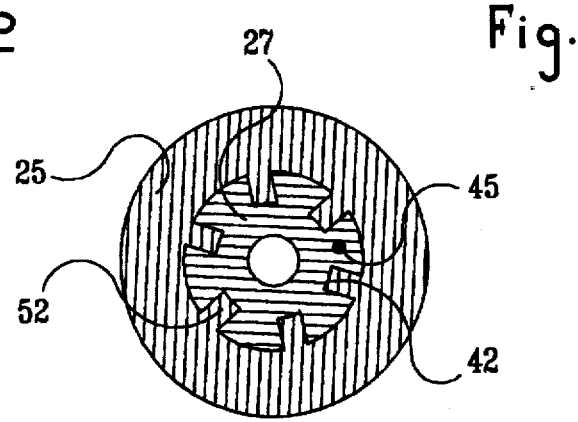
FIG. 4 is an enlarged cross sectional view along section line 4—4 of FIG. 1, showing the components of FIGS. 2 and 3 in assembled condition, as shown by FIG. 1.

The female socket 30 of the ejector tip holder 25 is formed to be approximately congruent with the cross sectional configuration of the ejector tip 27. As illustrated by FIG. 4, a vacuum-tight fit is thereby effected between the tip holder 25 and the ejector tip 27. Referring to FIGS. 3 and 4, slots 47 are configured to register with the ridges 43 of the tip 27 (FIG. 2), while bosses 52 are structured and arranged to register with matching grooves 42.

As best illustrated by FIG. 2, when a tip 27 is inserted into the mouth of a patient, the lips of the patient circumscribe the tip 27. Even with the lips pressed tightly against the outer surfaces of the ridges 43, however, the grooves 42 remain unblocked, and provide an air passage through the mouth. In this fashion, suction through the nozzle 28 is maintained, and the problem of backflow is avoided.

Reference in this disclosure to details of the preferred or illustrated embodiments is not intended to limit the scope of the claims, which themselves are intended to define the invention in terms of appropriate scope. It will be apparent to those skilled in the art, for example, that the surface of the tubular section 40 may be variously configured to interfere with effecting a sealing interface with the lips of a patient. For example, known extrusion techniques can impart a twist or spiral configuration to the grooves 42 and ridges 43. Known injection molding techniques can provide complimentary bosses 52 and slots 47 in a tip holder 25. A twisting press fit between such components would be satisfactory for purposes of this invention. Moreover, the construction details of the interface between the proximal end 29 of the tip 27 and the tip holder portion 25 of the ejector assembly 10 are not critical. Any practical arrangement which provides a vacuum-tight seal between the hand tool 21 and the tip 27 may be substituted for the socket arrangement illustrated.

What is claimed is:

1. A saliva ejector tip system, comprising:
   an ejector tip holder mountable to the distal end of a saliva ejector hand tool, whereby to present a socket at the distal end of said hand tool; and
   an ejector tip, having:
      a proximal end, insertable into said socket;
      a distal end, terminating in a suction-delivery element; and
      a tubular section between said proximal and distal ends of said ejector tip, having external surface configurations forming a means for interfering with a sealing interface between said tubular section and the lips of a patient circumscribing and pressed against said outer surface.

2. A system according to claim 1, wherein:
   said ejector tip has an internal bore extending its entire length;
   said tubular section extends to said proximal end;
   said outer surface configurations comprise structural elements of approximately constant cross sectional configuration, extending approximately parallel said bore to said proximal end; and
   the cross sectional configuration of said socket is approximately congruent with the cross sectional configuration of said proximal end.

3. A system according to claim 2, wherein said surface configurations are approximately linear grooves.

4. A system according to claim 3, wherein said socket carries bosses configured to register with said grooves, whereby to effect a vacuum-tight engagement.

5. A saliva ejector tip system, comprising:
   an ejector tip holder element carried at the distal end of a saliva ejector hand tool; and
   an ejector tip, having:
      a proximal end, adapted to couple with said tip holder element;
      a distal end; and
      a tubular section between said proximal and distal ends of said ejector tip, having external surface forming a means for interfering with a sealing interface between said tubular section and the lips of a patient circumscribing and pressed against said outer surface.

6. A system according to claim 5, wherein:
   said ejector tip has an internal bore extending its entire length;
   said tubular section extends to said proximal end;
   said external surface configurations comprise structural elements of approximately constant cross sectional configuration, extending approximately parallel said bore to said proximal end; and
   said holder element includes a socket approximately congruent with the cross sectional configuration of said proximal end.

7. A system according to claim 6, wherein said external surface configurations are approximately linear grooves.

8. A system according to claim 7, wherein said socket carries bosses configured to register with said grooves, whereby to effect a vacuum-tight engagement.

9. A saliva ejector tip system, comprising:

an ejector tip holder mountable to the distal end of a saliva ejector hand tool, whereby to present a socket at the distal end of said hand tool; and an ejector tip, having:
- a proximal end, insertable into said socket;
- a distal end, terminating in a suction-delivery element; and
- a tubular section between said proximal and distal ends of said ejector tip, having external surface configurations forming a means for interfering with a sealing interface between said tubular section and the lips of a patient circumscribing and pressed against said outer surface;

the surface of said socket being configured to register congruently with said tubular section at its said proximal end, whereby to effect a vacuum-tight engagement between said socket and said tubular section.

10. A saliva ejector tip system, comprising:

a saliva ejector hand tool carrying a socket at its distal end; and an ejector tip, having:
- a proximal end, insertable into said socket;
- a distal end, terminating in a suction-delivery element; and
- a tubular section between said proximal and distal ends of said ejector tip, said tubular section having external surface forming a means for interfering with a sealing interface between said tubular section and the lips of a patient circumscribing and pressed against said outer surface.

11. A saliva ejector tip system according to claim 10, wherein the surface of said socket is configured to register congruently with said tubular section at its said proximal end, whereby to effect a vacuum-tight engagement between said socket and said tubular section.

12. A saliva ejector tip system according to claim 10, wherein said surface configurations extend to said proximal end of said ejector tip.

* * * * *

UNITED STATES PATENT AND TRADEMARK OFFICE
CERTIFICATE OF CORRECTION

PATENT NO.   : 5,704,785
DATED        : January 6, 1998
INVENTOR(S)  : Young

It is certified that error appears in the above-identified patent and that said Letters Patent is hereby corrected as shown below:

On the cover page, under item "[56] References Cited" change "Coasd et al. to --Cosad et al.--.

Claim 9, line 10, after "surface" insert --configurations--;

Claim 10, line 10, after "surface" insert --configurations--.

Signed and Sealed this

Thirteenth Day of April, 1999

Attest:

Q. TODD DICKINSON

*Attesting Officer*        *Acting Commissioner of Patents and Trademarks*